United States Patent
Morgan et al.

(10) Patent No.: US 9,109,988 B2
(45) Date of Patent: Aug. 18, 2015

(54) CORROSION SENSORS

(75) Inventors: Peter Charles Morgan, Filton (GB); Michael Christopher Hebbron, Filton (GB)

(73) Assignee: BAE SYSTEMS plc, London (GB)

( * ) Notice: Subject to any disclaimer, the term of this patent is extended or adjusted under 35 U.S.C. 154(b) by 448 days.

(21) Appl. No.: 12/993,382

(22) PCT Filed: May 11, 2009

(86) PCT No.: PCT/GB2009/050492
§ 371 (c)(1),
(2), (4) Date: Feb. 2, 2011

(87) PCT Pub. No.: WO2009/141639
PCT Pub. Date: Nov. 26, 2009

(65) Prior Publication Data
US 2011/0187395 A1  Aug. 4, 2011

(30) Foreign Application Priority Data

May 20, 2008 (GB) .................................. 0809133.2
May 21, 2008 (EP) .................................. 08275019

(51) Int. Cl.
*G01R 27/08* (2006.01)
*B05D 5/12* (2006.01)
*G03F 7/20* (2006.01)
*G01N 17/04* (2006.01)

(52) U.S. Cl.
CPC ...................................... *G01N 17/04* (2013.01)

(58) Field of Classification Search
CPC ..................................................... G01N 17/04

USPC ......................................................... 324/700
See application file for complete search history.

(56) References Cited

U.S. PATENT DOCUMENTS

| | | | | |
|---|---|---|---|---|
| 4,238,298 | A | * | 12/1980 | Tsuru et al. ................. 205/775.5 |
| 4,782,332 | A | | 11/1988 | Cipris et al. |
| 5,306,414 | A | | 4/1994 | Glass et al. |
| 5,338,432 | A | * | 8/1994 | Agarwala et al. ............. 205/118 |
| 5,874,309 | A | | 2/1999 | Chang et al. |

(Continued)

FOREIGN PATENT DOCUMENTS

| | | |
|---|---|---|
| DE | 10 2007 010 780 A1 | 12/2007 |
| EP | 1 546 679 | 6/2005 |

(Continued)

OTHER PUBLICATIONS

Kallfass, et al., High voltage thin film transistors manufactured with photolithography and with Ta2O5 as the gate oxide, Thin Solid Films, vol. 61, Issue 2, Aug. 1, 1979, pp. 259-264, Abstract provided.*

(Continued)

*Primary Examiner* — Thomas F Valone
(74) *Attorney, Agent, or Firm* — Finch & Maloney PLLC (57) ABSTRACT

A corrosion sensor includes an insulating substrate, a thin film of a first metallic material formed on the substrate; and an array of areas what includes a second metallic material provided at the surface of the thin film. A method for manufacturing such a sensor is also disclosed. An exemplary embodiment is disclosed in which the thin film is patterned to define a number of tracks, the resistance of which can be monitored in order to determine the degree to which the thin film has corroded.

23 Claims, 3 Drawing Sheets

(56) References Cited

U.S. PATENT DOCUMENTS

| | | | |
|---|---|---|---|
| 6,383,451 B1* | 5/2002 | Kim et al. | 422/53 |
| 7,148,706 B2* | 12/2006 | Srinivasan et al. | 324/700 |
| 7,313,947 B2* | 1/2008 | Harris et al. | 73/86 |
| 2006/0002815 A1* | 1/2006 | Harris et al. | 422/53 |
| 2006/0162431 A1* | 7/2006 | Harris et al. | 73/86 |

FOREIGN PATENT DOCUMENTS

| | | |
|---|---|---|
| EP | 1 554 563 | 7/2005 |
| WO | WO 2004/031739 A2 | 4/2004 |
| WO | WO 2004/031740 A2 | 4/2004 |
| WO | WO 2004031739 A2 * | 4/2004 |

OTHER PUBLICATIONS

Montoya, et al., Influence of conductivity on cathodic protection of reinforced alkali-activated slag mortar using the finite element method, Corrosion Science, 51 (2009) p. 2857-2862.*

Bertolini et al., Cathodic protection of new and old reinforced concrete structures, Corrosion Science, V. 35, Issues 5-8, 1993, p. 1633-1639. Abstract provided.*

Harris et al., "A Corrosion Prediction Model and Corrosion Sensors for Corrosion Management" 1st World Congress on Corrosion in the Military, Jun. 1, 2005, 8 Pages.

Notification Concerning Transmittal of International Preliminary Report on Patentability (Forms PCT/IB/326 and PCT/IB/373) and the Written Opinion of the International Searching Authority (Forms PCT/ISA/237) issued in corresponding International Application No. PCT/GB2009/050492 dated Dec. 2, 2010.

International Search Report (PCT/ISA/210) issued on Aug. 10, 2009, by British Patent Office as the International Searching Authority for International Application No. PCT/GB2009/050492.

Search Report issued on Aug. 11, 2008, by European Patent Office for Application No. 08275019.1.

Search Report issued on Sep. 2, 2008, by British Patent Office for Application No. 0809133.2.

* cited by examiner

CORROSION SENSORS

FIELD

This invention relates to corrosion sensors for detecting the action of corrosive media acting on a metallic material when mounted in situ adjacent a location in the metallic material.

BACKGROUND TO THE INVENTION

Corrosion is a problem which leads to high maintenance and repair overheads in many different industries. Prompt detection of problems caused by corrosion is necessary in order for effective mitigation strategies to be put in place. Various different methods of detecting corrosion in a metallic material have been developed. Corrosion sensors have been developed that are able, for example, to detect corrosion, or to monitor the progress of corrosion, or to monitor the degradation of protective layers applied to corrosive surfaces.

A simple method to monitor corrosion is the visual inspection of a sample of the material of interest. Other sensors have been developed that are more appropriate for the through life monitoring of a structure. Such sensors can be readily interrogated to provide data relating to the Many of these known corrosion sensors rely on electrical measurements performed on a thin film of metallic material to determine the level of corrosion that has occurred to a structure. Two known types of corrosion sensor are described in the Applicant's published European Patent Applications, Publication Numbers EP1554563 and EP1546679. These prior-known sensors comprise patterned conductive thin films formed on a substrate. The film, which is made of a material that mimics the characteristics of the bulk material to which the sensor is attached, defines a plurality of serpentine tracks extending between common terminals. These sensors can be used as resistive sensors, in which case the resistance of the sensors is measured over a period of time. The result of the action of corrosive media on the tracks is an increase in the overall resistance of the sensor, as measured between the common terminals. This measured increase in resistance can then be related to the effects of corrosion acting on the bulk structure to which the sensor is attached.

A problem that exists in sensors of the above type is that it can be difficult to relate the sensitivity of the sensor to corrosive media to the sensitivity of the bulk structure to corrosive media. Where a sensor is used to monitor the progress of corrosion to a bulk structure, it is important that the sensor corrodes at a rate at least approximately equal to that at which the bulk structure corrodes; or alternatively that the rate at which the sensor material corrodes can be easily related to the rate at which the bulk structure corrodes. Whilst, in the above-referenced applications, it has been disclosed to configure the tracks in order to reduce geometric effects on the rate of corrosion of the tracks, it remains necessary to ensure that the thin film material closely mimics that of the bulk structure to which the sensor is attached. This is done firstly by using, for the thin film tracks, metallic material having the same composition as the alloy or metal from which the bulk structure is fabricated, and secondly by annealing the thin film in order to ensure that the microstructure of the thin film is at least approximately the same as that of the alloy or metal from which the bulk structure is fabricated.

An alternative corrosion sensing strategy is proposed in the paper "Corrosion Sensors in Platform Management" by D. G. Dixon, M. C. Hebbron, S. J. Harris and A. Rezai and presented at the 1$^{st}$ World Congress on Corrosion in the Military, 1$^{st}$ June 2005. The authors refer to the above-referenced published patent applications, and propose a similar resistive sensor. However, the sensor disclosed by Dixon et al. is covered with a corrosion-inhibiting primer paint that is provided with an intentional defect in order to mimic, for example, the effect of a crack. The sensor is located on the structure to be monitored. At first, the defect will be protected from corrosive media by inhibitor species leaching from the paint, but, once the reservoir of inhibitor is exhausted, the sensor tracks will corrode, and a corresponding increase in the sensor resistance can be measured. Corrective action can then be taken. Such sensors are also known as "Inhibitor Depletion Sensors".

In the case of an inhibitor depletion sensor, it is important that the resistive tracks beneath the defects corrode rapidly once the provisional protective effect of the inhibitor leaching from the paint has been exhausted, so that an operator can be made aware as quickly as possible that maintenance of the structure may be necessary. Thus there exists, in both cases, a need to be able to tailor the sensitivity of any particular type of corrosion sensor. The present invention arose as a result of consideration of the above-identified problems.

SUMMARY OF THE INVENTION

In accordance with a first aspect of the present invention, there is provided a corrosion sensor comprising: an insulating substrate; a thin film of a first metallic material formed on the substrate; and an array of areas comprising a second metallic material provided at the surface of the thin film. Herein, it should be understood that the term 'metallic' is used mean both alloys comprising one or more elementary metal components, and elementary metals. Galvanic corrosion is enhanced at the boundaries between the first and second metallic materials, and thus the sensitivity of the sensor can be tuned by altering the size and spacing of the metallic areas. Preferably, the areas are discrete areas. Routine experimentation can be used to determine the desired sensitivity, and thus the size and separation of the areas, for any particular application of the sensors.

The second metallic material may be more cathodic than the first metallic material. In exemplary embodiments described below, the second metallic material is selected such that, in use of the sensor, the second metallic material is cathodic relative to the first metallic material. Where the second metallic material is more cathodic than the first, galvanic corrosion of the first metal occurs. As those skilled in the art will appreciate, which metallic material of a pair of metallic materials is cathodic relative to the other may depend on the environment in which the sensor is placed, and thus the first and second metallic materials may preferably be selected in dependence on the application for which the sensor is to be used.

The areas may be formed on the surface of the thin film. Such an arrangement enables the sensors to be fabricated conveniently by deposition of a layer of the first metallic material, followed by a layer of areas of the second metallic material.

Preferably, electrical terminals are defined on the thin film such that an electrical property of the thin film can be monitored. The electrical property of the thin film may be the electrical resistance of the thin film. The electrical terminals may be protected from the effects of corrosion, for example by a layer of paint. The presence of terminals thus enables the corrosion of the sensor to be monitored remotely by monitoring of the electrical property. For example, the thin film may define a plurality of resistive tracks connecting the electrical terminals, and the areas comprising a second metallic material may be provided at the surface of the resistive tracks. This allows corrosion to be monitored by monitoring the resistance of the sensor. A layer of paint, such as a paint comprising a corrosion inhibitor, may cover the substantially the whole of the thin film, and the layer may define a plurality of defects arranged such that at least a part of each resistive track is exposed by one of the plurality of defects. Such a sensor is an improved version of the prior-known inhibitor depletion sensors, that can be used to monitor the protection provided to a structure by a layer of paint.

In one particular embodiment of an inhibitor depletion sensor, the thin film defines a plurality of conducting regions separate from the resistive tracks and the electrical terminals, the conducting regions being provided adjacent the resistive tracks. It has been determined empirically that the separation of the conducting regions from the resistive tracks can also be varied to control the sensitivity of the sensor to corrosive media. Such sensors are therefore more adaptable, since it is possible to vary its sensitivity both by variation of the size and spacing of the areas, and by variation of the separation of the conducting tracks from the conducting regions.

The areas may have a diameter in the range between 10 µm to 1 mm. The areas may be spaced apart by a distance no less than their diameter, and in the range between 10 µm to 1 mm.

The first metallic material may be aluminium. Aluminium is commonly used in aerospace applications. The second metallic material may is copper. Copper is commonly alloyed with aluminium in alloys for use in the aerospace industry. Where the first and second metallic materials are aluminium and copper respectively, the sensor can be used to mimic the behaviour of an aluminium and copper alloy.

Alternatively, the second metallic material is selected from the group consisting of silver and gold. Silver and gold are particularly noble metals, and thus their use as the second metallic material would result in particularly rapid corrosion of the first metallic material.

More generally, where the sensor is for use in monitoring the effects of corrosion on an alloy, the first metallic material may be the major constituent of the alloy, and the second metallic material may be a minor constituent of the alloy. The second metallic material may be a minor constituent that forms a second phase precipitate in the alloy. Galvanic corrosion can be accelerated around particles of a second phase precipitate in an alloy, and this effect can be mimicked on the sensor by appropriate selection of the first and second metallic materials. Notably, this obviates the need for deposition of a material mimicking the alloy. Instead, pure metals can be deposited, with the effect of the second phase precipitate mimicked by areas of the second phase precipitate metal deposited onto the thin film of the first metallic material.

The invention extends to a vehicle comprising a plurality of sensors as defined above.

In accordance with a second aspect of the present invention, there is provided a method of manufacturing a corrosion sensor comprising the steps of:

(i) providing an insulating substrate;
(ii) depositing a thin film of a first metallic material onto the insulating substrate; and
(iii) depositing areas of a second metallic material onto the thin film.

The method may further comprise the step of: (iv) removing material from the thin film to define resistive tracks. Conveniently, the step of removing material comprises removing material using photolithography.

BRIEF DESCRIPTION OF THE DRAWINGS

The above and further features of the invention are set forth with particularity in the appended claims and will be described hereinafter with reference to the accompanying drawings in which:

FIG. 3b is a detailed view of a part of the corrosion sensor illustrated in FIG. 3a.

DETAILED DESCRIPTION

The embodiments of the present invention described below are particularly suited to the monitoring of corrosion in alloys. Alloys are materials comprising one or more metallic components. Typically, an alloy will have one major component, and one or more minor components that are present in smaller quantities than the major component. For example, the 2000 series of aluminium alloys, widely used in the aerospace field, consist primarily of aluminium and copper, with copper present at a concentration of around 5% by weight. Other alloying constituents, such as magnesium, manganese, silicon, zinc, iron and chromium, may also be present in concentrations of less than 2% by weight. As another example, the 4000 series of aluminium alloys have a silicon constituent proportion forming in the region of 5%-20%, of the weight of the alloy.

It is possible to obtain a solid solution of copper in aluminium, such that a bulk sample of an aluminium and copper alloy can have a homogenous structure. However, more normally, a part of the copper constituent will be found as a second phase precipitate in the bulk alloy, forming crystallites of copper in a majority phase of aluminium/copper solid solution. The 2000 series of aluminium alloys exhibits this type of structure. The presence of the crystallites can improve the mechanical properties of the bulk alloy. However, the second phase precipitate can also affect the properties of the resulting alloy in the presence of corrosive media, such as sea water, or a salt spray. Galvanic corrosion occurs wherever two dissimilar metals are electrically connected in the presence of an electrolyte. One of the metals corrodes, whilst the other metal does not. The metal that corrodes is less noble than the metal that does not. Other terms are also used in the art instead of 'more noble' and 'less noble'. For example, metals are also described as 'less active' and 'more active'; or as 'anodic' and 'cathodic'. The more active or cathodic metal in any one electrically-connected pair of metals is that which corrodes is the presence of an electrolyte. Notably, in any pair of electrically connected metals, which metal is more noble than the other will depend on the electrolyte, or corrosive medium, to which the pair of metals is exposed. Considering specifically the 2000 series of aluminium alloys, copper is a more noble metal than aluminium in the presence of sea water, or spray from sea water. Thus the presence of copper crystallites in electrical contact with an aluminium/copper solid solution results in localised galvanic corrosion of the aluminium alloy, and can lead to the development of corrosion pits.

Figure 1:
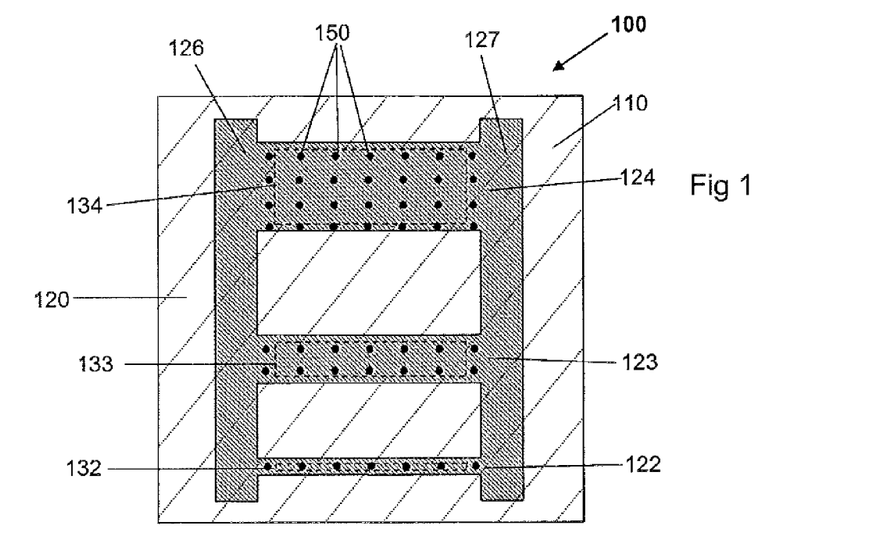
FIG. 1 is a schematic view corrosion sensor in accordance with a first embodiment of the invention.

Corrosion sensor 100 illustrated in FIG. 1 of the accompanying drawings is particularly designed for a 2000 series aluminium alloy. Sensor 100 illustrated in FIG. 1 of the accompanying drawings is of the inhibitor depletion type described in the above-referenced paper "Corrosion Sensors in Platform Management" by D. G. Dixon, M. C. Hebbron, S. J. Harris and A. Rezai, and comprises a substrate 110, a patterned conductive thin film 120, and paint substantially covering the substrate 110 and the patterned conductive thin film 120. The area covered by the conductive thin film is indicted by dense shading, whilst that covered by paint is indicated by more sparse shading. The film 120 is arranged in a ladder-like configuration such that there are three tracks 122, 123, 124 running between common terminals 126 and 127. Three defects 132, 133, and 134 are introduced into paint 130, with each defect being provided at the location of one of the tracks 122, 123, and 124. The defects are areas where the protective layer of paint has been removed. However, in the case of an as-fabricated sensor, these areas remain temporarily protected from the effects of corrosion because of the effect of inhibitor ions leaching out of the surrounding paint and onto the area of the defect. The tracks 122, 123, 124 are arranged to be wider than their respective defects 132, 133, 134 such that the entire exposed area beneath each defect consists of metallic track material. Each defect is of a different size. For example, the defect widths can be chosen to be 4 mm, 0.5 mm, and 0.05 mm.

The conductive thin film 120 is formed on the substrate 110 by sputtering. In the present embodiment, where the sensor is for application to a structure formed of a 2000 series aluminium alloy, the film is formed of aluminium. The film is patterned either by masking during sputtering, or by photolithography subsequent to the deposition of the thin film. An array of copper dots 150 is then deposited, again by sputtering, on each of the tracks 122, 123, and 124. The copper dots form an array of areas of a different metallic material to the aluminium. The dots may be circular, as shown in FIG. 1, but could be of any desired shape—for example, it may be preferred to deposit hexagonal dots. The dots 150 act as centres for galvanic corrosion, mimicking the effect of copper crystallites in the bulk alloy, and enhancing the sensitivity of the tracks 122, 123, and 124 to corrosion.

In the present embodiment, the sensitivity to corrosion of the aluminium thin film 120 can be tailored by appropriate choice of the size and spacing of the copper dots 150. The selection of size and spacing of the dots in the array 150 can be readily made by those skilled in the art by experimental comparison of the rate of corrosion a number of samples of thin film material 120, each having a different dot size and spacing to the others, with a sample of the bulk material. The diameter and spacing of the dots may be in the range 10 µm to 1 mm; for example, the diameter of the dots may be 250 µm, and their spacing may be 1 mm.

Paint is applied over the conductive thin film using a mask to define the defects 132, 133, and 134. Alternatively, chemical and dry etching techniques are possible. Suitable chemical etchants and masks can be chosen in dependence on the type of paint used. The paint is of the same type as that covering the bulk structure which the corrosion sensor 200 is to monitor, or may be of a type mimicking that covering the bulk structure. In the present embodiment, a 25 µm thick coating of PR205, a primer paint commercially available from PRC DeSoto, is used. PR205 is a high-solids, chromate-loaded, epoxy-based primer. A suitable topcoat, such as HP03682, also available from PRC DeSoto, is then applied. One etchant that can be used for these paints is ethylene glycol. Using these techniques, defects having widths between 50 µm and 8 mm can be fabricated.

In use, the resistance of the sensor 100 between points 150 is monitored over time. The resistance of the sensor remains approximately constant until the protective effect of inhibitor leaching from the paint around the largest defect 134 ceases, because of exhaustion of the reservoir of inhibitor ions in the primer paint. At this point, the resistance will begin to increase as a result of corrosion depleting the amount of material in the conductive track 124. This, in turn, indicates when corrosion will begin to affect metal in other parts of the structure where there may be similar defects. By introducing a number of differently-sized defects, each over one rung of the ladder, a measure of the continuing effects of corrosion is obtained: the track beneath the largest defect 124 will corrode first, followed by that under the intermediate-sized defect 123, followed by that under the smallest-sized defect 122.

It will therefore be appreciated that it is convenient for tracks 122, 124, and 124 to corrode in a manner similar to, or more rapidly than, that of the bulk alloy the corrosion of which the sensor is intended to monitor. The application of copper dots 150 enables the rate at which the corrosive thin film tracks corrode to be adjusted so as either to more closely mimic the behaviour of the bulk alloy, or so as to corrode more rapidly than the bulk alloy.

Figure 2:
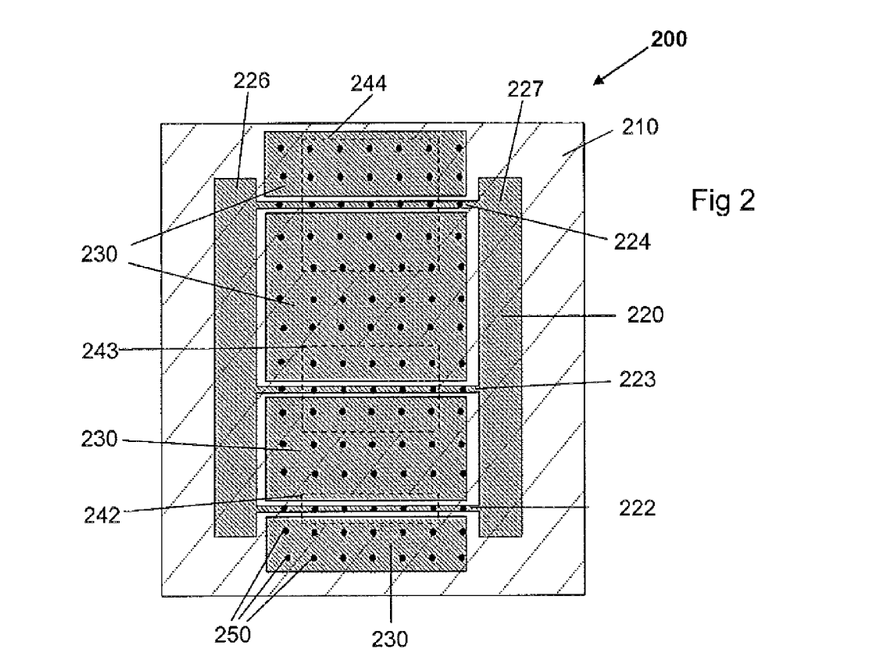
FIG. 2 is a schematic view of a corrosion sensor in accordance with a second embodiment of the invention.

The application of copper dots to thin film tracks can be used to tune the sensitivity of a number of different types of corrosion sensor that rely on measurements of the resistance of a thin film of aluminium or aluminium alloy, in generally the same manner as is described above with reference to the first embodiment 100. A corrosion sensor 200 in accordance with a second embodiment of the invention is illustrated in FIG. 2. Corrosion sensor 200 functions in broadly the same manner as corrosion sensor 100 illustrated in FIG. 1, and is fabricated in a manner similar to that described above with regard to corrosion sensor 100. Corrosion sensor 200 is also intended for the monitoring of a painted structure formed from an aluminium alloy with a predominant minor component of copper. Sensor 200 comprises a substrate 210 and a patterned conductive thin film 220, 230. Film 220 is arranged in a ladder-like configuration such that there are three tracks 222, 223, 224 (that form the "rungs" for the ladder) running between common terminals 226, 227 (that form the "legs" for the ladder). In use of the sensor, electrical connections are made to the sensor from interrogating instrumentation via the common terminals 226, 227. In addition to the ladder-like configuration 220, there are also provided separate conducting regions 230. These conducting regions are located between conducting tracks 222 and 223, between conducting tracks 223 and 224, above (as shown in FIG. 2) conducting track 222, and below (as shown in FIG. 2) conducting track 224. The separate conducting regions 230 are positioned closely adjacent the conducting tracks 222, 223, 224, without making electrical contact with the ladder like configuration 220. Thus, there is a conducting region on either side of each conducting track, with a small gap between the conducting track and each conducting region. There is a further small gap between the conducting regions 230 and the common terminals 226, 227. The gap on either side of the conducting track is of uniform width along the entire length of the conducting track, except for those parts of the conducting tracks close to the common terminals 226, 227.

As for corrosion sensor 100 illustrated in FIG. 1, the thin film conducting tracks are made of aluminium, and copper dots 250 are applied to the thin film conducting tracks 222, 223, 224, and the thin film conducting regions 230, after their deposition. The copper dots, as in the case of the first embodiment, serve to mimic the effect of copper crystallites present in the bulk alloy, and enhance the rate of galvanic corrosion of the thin film. The dots are of a size in the range 10 µm to 1 mm, and are spaced apart by a distance in the range 10 µm to 1 mm. As described above with regard to the first embodiment, the size and spacing of the dots 250 can be varied in order to tune the sensitivity of the sensor 200 to corrosion, such that it matches the sensitivity of a bulk sample. The copper dots 250 are provided on both the conducting tracks 222, 223, 224, and the conducting regions 230, so that the properties of those parts of the surface exposed to the ambient corrosive environment remain uniform.

Paint is applied to the surface of the sensor once the thin film and copper dots have been deposited, and covers the surface of the sensor 200 except for defects 242, 243, and 244 over each of the conducting tracks 222, 223, and 224, and extending over part of the conducting regions 230. The extent of the paint coverage, as in FIG. 1, is illustrated in FIG. 2 by the sparse shading, whilst the location of the metallic thin film is illustrated by the more densely-shaded regions. The paint used for sensor 200 is the same as that used for sensor 100.

Sensor 200 is used in a manner very similar to sensor 100: the resistance of the sensor is monitored to determine when the protective effect of inhibitor leaching from the paint over the defects 242, 243, and 244 ceases. The main advantages of sensor 200 over sensor 100 are its higher resistance, due to the smaller cross-sectional area of the conducting tracks 222, 223, 224 in comparison to tracks 122, 123, 124 of sensor 100; and the fact that the tracks 222, 223, 224 will corrode completely through—whereas tracks 122, 123, 124 will not, since their edges remain partly protected by paint—so that a larger change in resistance occurs for sensor 200 than for sensor 300 when provisional protection ceases. Moreover, the sensitivity of the sensor 200 to corrosion can be adjusted both by the variation of the size and spacing of the dots 250, and by the spacing of the gaps between the conducting regions 230 and the conducting tracks 222, 223, and 224: it has been found empirically that the time to corrosion of the tracks 222, 223, and 224 decreases as the gap width is decreased.

In each of the above described embodiments, the presence of copper dots formed on the surface of a thin film is used to adjust the sensitivity of a thin film of metallic material to corrosion. As will be appreciated by those skilled in the art, in the case of inhibitor-depletion sensors such as the corrosion sensors 100 and 200 illustrated in FIGS. 1 and 2, it may be desired that the corrosive tracks corrode through rapidly once the protective effect of leaching inhibitor has ceased. Therefore, it may be convenient to form a high density array of copper dots on the thin film corrosive tracks in order to accelerate their corrosion. An alternative manner in which the sensitivity to corrosion of the thin film track can be enhanced is by careful selection of the material used for the dots: the more noble the metal used to form the dots, the stronger will be the enhancement in the rate of galvanic corrosion of the surrounding thin film. Thus, where a high rate of galvanic corrosion of the thin film material is desired, a strongly cathodic metal may be used to form the dots, such as silver or gold.

Figure 3A:
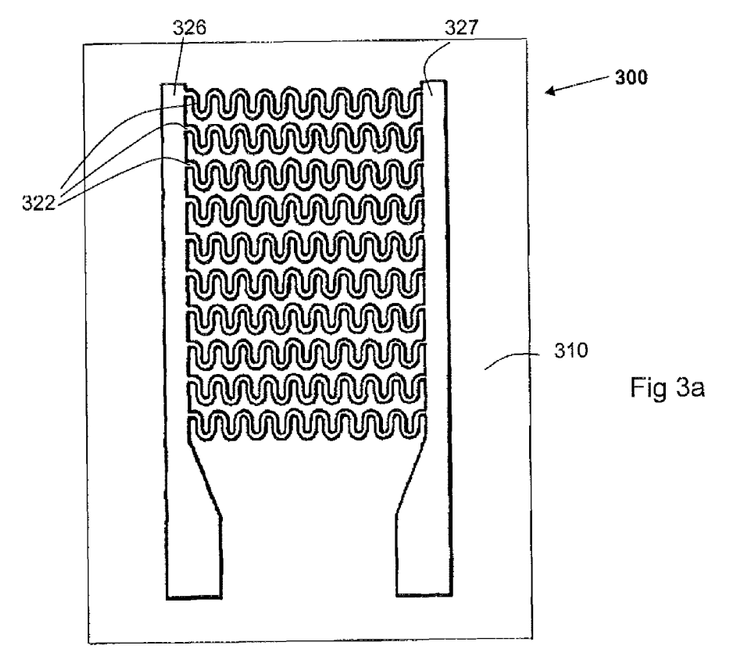
FIG. 3a is a schematic view of a corrosion sensor in accordance with a third embodiment of the invention.
Figure 3B:
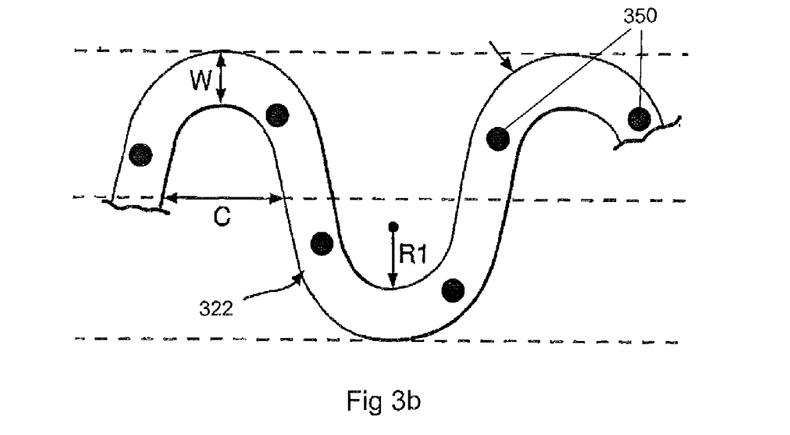

A corrosion sensor 300 in accordance with a third embodiment of the invention is illustrated in FIGS. 3a and 3b. Sensor 300 is fabricated for the monitoring of corrosion to a 2000 series aluminium alloy and is a simple resistance sensor, of the type described in European Patent Application Publication Number 1554563. As shown in FIG. 3a, sensor 300 comprises a conductive thin film 320 deposited on an insulating substrate 310. Conductive thin film forms common terminals 326, 327, and a plurality of conducting tracks 322 running between the common terminals. The conductive tracks are exposed to the ambient corrosive environment, and not covered by any protective paint (in contrast to sensors 100 and 200 described above). Corrosion is monitored by monitoring the electrical resistance between the common terminals 326, 327. The resistance of the sensor increases as the tracks corrode in the corrosive environment. Because a number of tracks 322 are included between the common terminals 326, 327, and the tracks are arranged in parallel, the effect of localised corrosion, such as pitting corrosion, can be monitored as an average across all the tracks 322. Moreover, the geometry of each of the tracks 322 is carefully controlled in order to ensure that geometric effects do not appreciably affect the rate of corrosion of the thin film 320, and so that the resistance of the sensor 300 can be related to the effect of corrosion on the bulk structure. This carefully controlled geometry is described in detail in European Patent Application Publication Number 1554563.

A section of one exemplary track 322 is shown in FIG. 3b. Track 322 is of substantially constant width W, and is formed to meander across a linear corridor 340 defined on the substrate 310. The corridor 340 has a width D2, within which the meanders of corrosive track 322 are contained. The track formed of a series of generally U-shaped bends alternately of opposite curvature, resulting in a repeating serpentine shape within the linear corridor 340. Corrosive track 322 is formed of aluminium, and copper dots 350 are formed on the surface of the corrosive tracks 322, as is shown most clearly in FIG. 3b, in order to mimic the effect of copper crystallites in the bulk alloy that enhance the rate of galvanic corrosion. As in the first and second embodiments described above, the size and spacing of the dots can be selected such that the response of the corrosive tracks 322 to corrosive media mimics closely the response of the bulk aluminium alloy to corrosive media. Those skilled in the art will appreciate that the careful adjustment of the sensitivity to corrosion of sensor 300 is more important that that of sensors 100 and 200 described above. In sensors 100 and 200, deterioration in the condition of the paint is sensed, and it is desirable for the sensors to produce a measurable response as soon as the protective effect of the paint ceases: thus, it is of limited consequence if the corrosive tracks of sensors 100 and 200 corrode more rapidly than the bulk structure. However, for sensor 300, it is the corrosion of the tracks 322 themselves that provides the measurable response of the sensor to corrosion, and it is therefore more important that the sensor accurately reflects the condition of the bulk structure. The provision of dots 350 enables the sensitivity of the tracks 322 to corrosion to be carefully adjusted, by routine experimentation to determine the appropriate size and spacing of the dots 350.

Fabrication of sensor 300 is performed as described for the prior known sensors disclosed in European Patent Application Publication Number 1554563. It is to be noted that this method of fabrication includes a step of annealing the as-sputtered conductive thin films. In order to improve the degree to which the corrosive characteristics of the thin film tracks mimic the bulk alloy, the thin film layer is annealed following sputtering to encourage growth of metallic grains within the thin layer to produce a thin film which is essentially a two-dimensional array of metallic grains, in order to ensure that the conductive thin film on the sensors has a similar microstructure to that of the bulk structure which the sensor is designed to monitor. In the case of sensor 300, this step can be omitted, since the sensitivity to corrosion of the thin film can be altered by alteration of the size and spacing of the copper dots 350.

It is to be noted that, for each of the corrosion sensors 100, 200, 300 described above, electrical terminals (not shown in the figures) are formed on the common terminals (126, 127; 226, 227; 326; 327) such that the sensors can be connected to external apparatus in order to measure the resistance of the sensors. Such terminals are areas where electrical connections, for example by soldering or otherwise bonding wire to the thin film, can be made to the sensors. It is also to be noted that, in each of the above-described embodiments, the substrate can be formed from any suitable insulating material on which a thin film of the track material can be deposited. For example, Mylar™, or polyimide can be used. Alternatively, a conducting substrate coated with an insulating layer of, for example, polyimide can be used.

Figure 4:
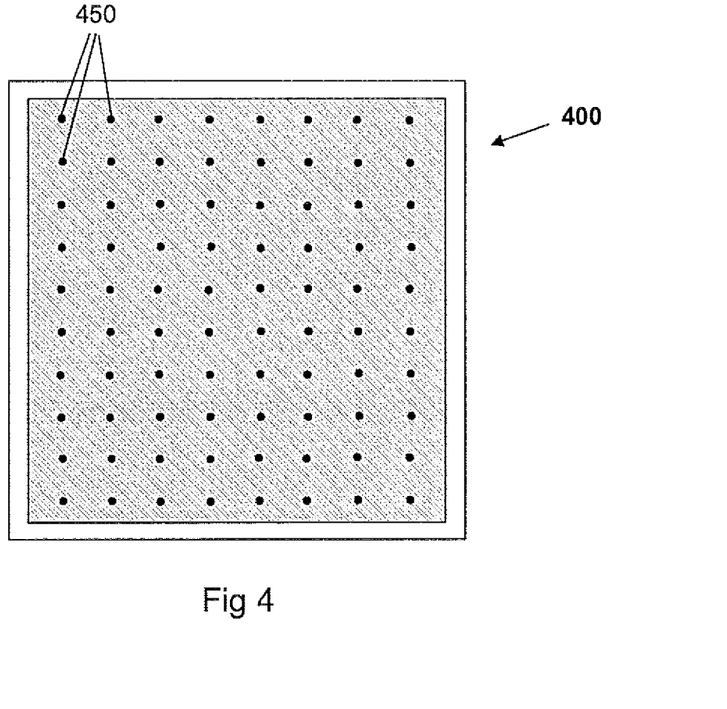
FIG. 4 is a schematic view of a corrosion sensor in accordance with a fourth embodiment of the invention.

The use of dots of a second metallic material formed on the surface of a thin film of a first metallic material can also be applied to corrosion sensors other than those that use electrical measurements to determine the degree of corrosion affecting a structure. A corrosion sensor 400 in accordance with a fourth embodiment of the invention, also for use in monitoring the effect of corrosive media on a 2000 series aluminium alloy, is shown in FIG. 4. Sensor 400 comprises a thin film of aluminium deposited on a substrate 410, and an array of copper dots 450 formed on the surface of the thin film. Dots 450 are formed of a size and at a spacing similar to those described above with reference to the first, second and third embodiments of the invention. However, corrosion sensor 400 does not require electrical interrogation in order to determine an electrical property of the thin film, such as its resistance, but instead is designed to be visually inspected, either by microscope (where the dots are of a small diameter—for example 10 μm), or by eye (where the dots are of a larger diameter—for example 1 mm). It is envisaged that such an arrangement may be particularly useful in the case where it is desired to test a variety of samples of sensors in the laboratory in order to determine the best possible size and spacing for the dots on a sensor such as sensors 100, 200, or 300 described above; although those skilled in the art will appreciate that such sensors could also be of use in other environments.

Sensor 400 is fabricated by deposition of a thin film layer of aluminium onto a substrate, preferably by sputtering. The substrate can be of any convenient material that is suitable for use in a sputtering chamber—it is not necessary for the substrate to be insulating in the case of sensor 400. The array of dots 450 is then deposited on the surface of the thin film layers, again preferably by sputtering, with a mask to define the size and spacing of the dots.

The thickness of the corrosive tracks is selected in accordance with the material from which the tracks are formed and the type of application for the microsensor. For example, for monitoring components in a marine environment the rate of corrosion is relatively high, and therefore a relatively thick film is used, for example, in the case of an aluminium alloy, corrosive tracks in the region of 50 μm to 500 μm in thickness are used. However, for other applications in which the environment in which the microsensor is to be placed is less corrosive, higher sensitivity to corrosion is required, and therefore thinner films are used to form the corrosive tracks. In the case of monitoring non-marine aircraft components, the thickness of the corrosive tracks is preferably between 0.5 μm and 10 μm, for example approximately 1.5 μm. The thickness of the dots in each of the above-described embodiments is similar to the thickness of the as-sputtered thin film.

Having described the invention with reference to various specific embodiments, it is noted that these embodiments are in all resects exemplary. Variations and modifications are possible without departing from the scope of the invention, which is defined in the accompanying claims. Such variations and modifications will be immediately obvious to those skilled in the art. For example, whilst in the above, it has been described to use straight conducting tracks between conducting terminals of sensors 100 and 200, it will be understood by those skilled in the art that it is possible to use tracks of a different configuration, such as the serpentine tracks described with regard to corrosion sensor 300 in accordance with the third embodiment of the invention. In the case of sensor 200, optionally, such serpentine tracks could be used in conjunction with complementarily shaped conducting regions. The shape of the dots applied to the thin film of aluminium can also be modified. It may be preferred to deposit, for example, hexagonal-shaped dots. The shape of the dots may be chosen for convenience for a given fabrication technique. Moreover, it may be desired to deposit stripes of copper across resistive tracks (particularly in the case of sensors 100 and 200) in order to ensure that a break in the resistive track is formed quickly, resulting in a large change in the resistance measured across the electrical terminals. Furthermore, whilst it has been described above that the dots are preferably of a uniform size and spacing, it is noted that both regular and irregular arrays of dots are envisaged, since it is currently thought that the effect of the dots on the properties of the alloy will be dominated by their average size and spacing. Regular arrays of dots may be formed based on a number of different patterns, for example to improve the rotational symmetry of the sensor.

Furthermore, whilst in the above it has been described that the thin films and dots of corrosion sensors 100, 200, 300 and 400 are formed of aluminium and copper respectively, and that the sensors are for use in monitoring the effects of corrosion on 2000 series aluminium alloys, it is to be noted that the present invention can readily be applied using other metallic materials, in dependence on the particular platform on which the sensors are to be used, the materials from which that platform is made, and the environment in which it is to be operated. The 2000 series aluminium alloys are in widespread use in aircraft, and so these sensors are expected to find application in health monitoring systems for aircraft. However, it is anticipated that, by substitution of appropriate metals for the aluminium and copper in sensors 100, 200, 300, and 400, embodiments of the invention could be made that are applicable to platforms made from different materials. In most cases, it is considered desirable that the metal from which the dots are fabricated is more noble than the metal from which the film is fabricated. In this way, it is the film that corrodes, and not the dots, resulting, in the case of sensors 100, 200, and 300, in a measurable variation in the conductivity of the sensor. In such examples, if the dots are less noble than the film, the dots will corrode, and there will be little measurable effect on the resistance of the sensor. In the case of sensor 400, such considerations are not relevant, it being necessary only that visual inspection of the sensor reveals any effects of corrosion.

The determination of which metal of a pair of metals is the more noble in the presence of a particular electrolyte can be made with reference to a galvanic series. Galvanic series list metals in order of the nobility as measured in the presence of a particular electrolyte. One exemplary galvanic series is set out in MIL-STD-889, a military standard published by the US Department of Defence entitled "Dissimilar Metals", and lists a number of metals (including alloys) in order of their nobility in the presence of sea water, from the most noble to the least noble. Where pairs of metals selected from those listed are in electrical contact in the presence of sea water, the metal closest to the 'active' or 'less noble' end of the list will galvanically corrode.

Of course, it may be desirable to use a second metallic material for the dots that is different to any alloying constituent, in order to enhance the corrosion rate of the thin film—for example, a noble metal such as gold could be used for the dots.

It is also possible to modify the sensors 100, 200, 300 as described above such that the substrate is almost entirely covered with the conductive thin film. Such a modification ensures that the paint will stick to the sensor more uniformly.

As those skilled in the art will appreciate, paint will not stick to the material of the substrate to the same degree that it will adhere to the conductive thin film, and therefore, by ensuring that the substrate is substantially entirely covered with the conductive film (leaving only gaps to define the conducting tracks 222, 223, 224 and terminals 226, 227, in the example of sensor 200), it can be ensured that the sensor mimics more closely the behaviour of the bulk structure.

Those skilled in the art will also appreciate that, whilst it has been described in the above to use commercially available paints for sensors 100 and 200, it may be necessary, where such sensors are to be retro-fitted to existing vehicles, to mix paint with an appropriate inhibitor ion concentration, in order to mimic the effect of the age of the paint on the structure to be monitored. It is also noted that paints comprising corrosion inhibitors are widely available from a number of manufacturers, including Akzo Nobel, Anac, and Indestructible Paints, which manufacturers are able to supply equivalents to the PR205 primer paint used in the above-described embodiments of the invention. Moreover, it is also envisaged to use paints comprising corrosion inhibitors other than chromate ions. Such paints are expected to become more widely used in the future because of the potential hazards of chromate-containing paints.

Those skilled in the art will also appreciate that any discrete areas of a second metallic material may be used instead of dot-like areas. It may beHowever, sensors in which areas other than dots of the second metallic material are used are envisaged, and in such cases it may be desirable for the second material to be less noble than the first.

Finally, it is noted that it is to be clearly understood that any feature described above in relation to any one embodiment may be used alone, or in combination with other features described, and may also be used in combination with one or more features of any other of the embodiments, or any combination of any other of the embodiments.

The invention claimed is:

1. A corrosion sensor comprising:
    an insulating substrate;
    a thin film of a first metallic material formed on the substrate, the thin film constructed and arranged in a ladder-like configuration including a plurality rung-like features;
    an array of separate areas comprising a second metallic material, positioned on the plurality of rung-like features;
    a plurality of electrical terminals defined by the thin film for monitoring electrical resistance of the thin film; and
    a plurality of resistive tracks defined by the rung-like features of the thin film, at least portions of the plurality of resistive tracks providing a plurality of separate electrical pathways between the electrical terminals, wherein the separate areas comprising the second metallic material are provided at surfaces of the portions of the plurality of resistive tracks that provide the plurality of separate electrical pathways for enhancing a rate of galvanic corrosion of the thin film.

2. A corrosion sensor as claimed in claim 1, wherein the second metallic material is selected such that the second metallic material will be cathodic relative to the first metallic material during sensor operation.

3. A corrosion sensor as claimed in claim 1, wherein the electrical terminals are protected from effects of corrosion.

4. A corrosion sensor as claimed in claim 3, wherein the electrical terminals are protected from the effects of corrosion by a layer of paint.

5. A corrosion sensor as claimed in claim 1, wherein a layer of paint covers the thin film, the layer defining a plurality of defects arranged for exposing at least a part of each resistive track by one of the plurality of defects.

6. A corrosion sensor as claimed in claim 5, wherein the paint comprises a corrosion inhibitor.

7. A corrosion sensor as claimed in claim 6, wherein the thin film defines a plurality of conducting regions separate from the resistive tracks and the electrical terminals, the conducting regions being provided adjacent the resistive tracks.

8. A corrosion sensor as claimed in claim 1, wherein the areas have a diameter in the range between 10 μm to 1mm.

9. A corrosion sensor as claimed in claim 1, wherein the areas are spaced apart by a distance no less than their diameter, and in a range between 10 μm to 1mm.

10. A corrosion sensor as claimed in claim 1, wherein the first metallic material is aluminum.

11. A corrosion sensor as claimed in claim 1, wherein the second metallic material is copper.

12. A corrosion sensor as claimed in claim 1, wherein the second metallic material is selected from the group consisting of silver and gold.

13. A corrosion sensor as claimed in claim 1 for monitoring. effects of corrosion on an alloy, wherein the first metallic material is a major constituent of the alloy to be monitored, and wherein the second metallic material is a minor constituent of the alloy.

14. A corrosion sensor as claimed in claim 13, wherein the second metallic material forms a second phase precipitate in the alloy.

15. A corrosion sensor as claimed in claim 1, wherein each area in the array of separate areas is a dot.

16. A corrosion sensor as claimed in claim 1, wherein at least some of the resistive tracks of the plurality of physically separate electrical pathways have different sensitivities to corrosion.

17. A corrosion sensor as claimed in claim 1, wherein the array of separate areas comprising the second metallic material includes areas of different sizes.

18. A vehicle comprising a plurality of corrosion sensors, each corrosion sensor comprising:
    an insulating substrate;
    a thin film of a first metallic material formed on the substrate the thin film constructed an arranged in a ladder-like configuration including a plurality of rung-like features;
    an array of separate areas comprising a second metallic material positioned on the plurality of rung-like features;
    a plurality of electrical terminals defined by the thin film for monitoring electrical resistance of the thin film; and
    a plurality of resistive tracks defined by the rung-like features of the thin film, at least portions of the plurality of resistive tracks providing a plurality of separate electrical pathways between the electrical terminals, wherein the separate areas comprising the second metallic material are provided at surfaces of the portions of the plurality of resistive tracks that provide the plurality of separate electrical pathways for enhancing a rate of galvanic corrosion of the thin film.

19. A corrosion sensor as claimed in claim 18, wherein the array of separate areas comprising the second metallic material includes areas of different sizes.

20. A method of manufacturing a corrosion sensor, comprising:
    providing an insulating substrate;

depositing a thin film of a first metallic material onto the insulating substrate, the thin film constructed and arranged in a ladder-like configuration including a plurality of runt like features;

defining a plurality of electrical terminals on the thin film for monitoring electrical resistance of the thin film;

defining a plurality of resistive tracks on the rung-like features of the thin film at least portions of the plurality of resistive tracks providing a plurality of separate electrical pathways connecting the electrical terminals; and depositing areas of a second metallic material onto surfaces of the portions of the plurality of resistive tracks on the rung-like features that provide the plurality of separate electrical pathways for enhancing a rate of galvanic corrosion of the thin film.

21. A method as claimed in claim 20, comprising:

removing material from the thin film to define the resistive tracks.

22. A method as claimed in claim 21, wherein the removing of material comprises:

removing material using photolithography.

23. A method as claimed in claim 20, wherein the areas of the second metallic include areas of different sizes.

\* \* \* \* \*